US010525006B2

(12) United States Patent
Lewis et al.

(10) Patent No.: US 10,525,006 B2
(45) Date of Patent: *Jan. 7, 2020

(54) PHARMACEUTICAL SOLUTION FORMULATIONS FOR PRESSURISED METERED DOSE INHALERS

(71) Applicant: CHIESI FARMACEUTICI S.P.A., Parma (IT)

(72) Inventors: David Andrew Lewis, Parma (IT); Brian John Meakin, Parma (IT); Gaetano Brambilla, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/353,978

(22) Filed: Nov. 17, 2016

(65) Prior Publication Data

US 2017/0065518 A1 Mar. 9, 2017

Related U.S. Application Data

(63) Continuation of application No. 12/255,075, filed on Oct. 21, 2008, which is a continuation of application No. PCT/EP2007/003420, filed on Apr. 19, 2007, which is a continuation of application No. 11/408,026, filed on Apr. 21, 2006, now abandoned.

(51) Int. Cl.
| | |
|---|---|
| *A61K 9/00* | (2006.01) |
| *A61K 31/167* | (2006.01) |
| *A61K 31/58* | (2006.01) |
| *A61K 47/10* | (2017.01) |
| *A61K 9/12* | (2006.01) |
| *A61K 31/138* | (2006.01) |
| *A61K 31/4745* | (2006.01) |
| *A61K 31/57* | (2006.01) |
| *A61K 31/573* | (2006.01) |
| *A61K 45/06* | (2006.01) |
| *A61K 31/4704* | (2006.01) |

(52) U.S. Cl.
CPC .............. *A61K 9/008* (2013.01); *A61K 9/124* (2013.01); *A61K 31/138* (2013.01); *A61K 31/167* (2013.01); *A61K 31/4704* (2013.01); *A61K 31/4745* (2013.01); *A61K 31/57* (2013.01); *A61K 31/573* (2013.01); *A61K 31/58* (2013.01); *A61K 45/06* (2013.01); *A61K 47/10* (2013.01)

(58) Field of Classification Search
CPC .. A61K 31/167; A61K 31/4704; A61K 31/58; A61K 45/06; A61K 47/10; A61K 9/008; A61K 31/573; A61K 9/124
See application file for complete search history.

(56) References Cited

U.S. PATENT DOCUMENTS

| | | | |
|---|---|---|---|
| 5,483,953 A | 1/1996 | Cooper | |
| 5,972,919 A | 10/1999 | Carling et al. | |
| 6,585,958 B1 | 7/2003 | Keller et al. | |
| 6,713,047 B1 | 3/2004 | Lewis et al. | |
| 6,716,414 B2 | 4/2004 | Lewis et al. | |
| 6,964,759 B2 | 11/2005 | Lewis et al. | |
| 7,018,618 B2 | 3/2006 | Lewis et al. | |
| 7,601,336 B2 | 10/2009 | Lewis et al. | |
| 8,088,362 B2* | 1/2012 | Church | A61K 9/008 424/45 |
| 8,313,732 B2* | 11/2012 | Davies | A61K 9/008 424/45 |
| 10,098,837 B2* | 10/2018 | Scuri | A61M 15/0021 |
| 2005/0201951 A1 | 9/2005 | Barr et al. | |
| 2006/0120966 A1 | 6/2006 | Church et al. | |
| 2006/0198896 A1 | 9/2006 | Liversidge | |
| 2009/0263488 A1 | 10/2009 | Davies et al. | |
| 2011/0061651 A1 | 3/2011 | Davies et al. | |

FOREIGN PATENT DOCUMENTS

| | | |
|---|---|---|
| EP | 1 157 689 A1 | 11/2001 |
| WO | 99/65460 | 12/1999 |
| WO | 00/06121 | 2/2000 |
| WO | 00/53187 | 9/2000 |
| WO | 01/89480 A1 | 11/2001 |

OTHER PUBLICATIONS

J. Bousquet et al., Original Research Article, Clin. Pharmacokinet (2009) vol. 48 No. 6 pp. 347-358.
V. Muller et al., BMC Pulmonary Medicine, (2011) vol. 11, pp. 1-8.
Guidelines for the Diagnosis and Management of Asthma, NIH, 2007.
P.M.A. Calverley et al., Respiratory Medicine, vol. 104, pp. 1858-1868 (2010).
Medicines Compedium 2004, Datapharm Communications (2004).
Physicians' Desk Reference, Thomson PDR, Montvale, NJ , pp. 3518, (2007).
H. Koyama et al., Nihon Kyobu Shikkan Gakki Zasshi, 33(4), p. 410-415 (1995) Abstract only.
C. P. van Schayck et al., Chest, 107(5), 1199-1205 (1995).
K. Nishimura et al., Chest, 115(1), pp. 31-37 (1999).
Physicians Desk Reference, 58th Ed., 2004, pp. 1740-1741.
Medicines Compendium 2004, Datapharm Communications Ltd., Surrey, England, 2004, entries for Symbicort 100/6 Turbohaler and Symbicort 200/6 Turbohaler.
H.Y. Park, BMJ, 2012;345:e6843 doi.

(Continued)

*Primary Examiner* — Mina Haghighatian
(74) *Attorney, Agent, or Firm* — Oblon, McClelland, Maier & Neustadt, L.L.P.

(57) ABSTRACT

The invention relates to the prevention and/or treatment of a severe broncho-pulmonary disease by administering a solution formulation from a pressurized metered dose inhaler capable of providing therapeutic doses of two or more active drug substances to the lung, wherein all the active drug substances are fully dissolved in the formulation as well as the two or more active drug substances are delivered with substantially the same particle size distribution.

7 Claims, 2 Drawing Sheets

(56) References Cited

OTHER PUBLICATIONS

Global Initiative for Chronic Obstructive Lung Disease, 2011, pp. 12-14.
Symbicort Turbohaler 200/6 Inhalation Powder 2013.
Symbicort 160/45 2012.
C.L. Leach et al., *Eur. Respir. J.*, vol. 12, p. 1346-1353 (1998).
S. Wang et al., *The Journal of Immunology*, vol. 166, pp. 2741-2749 (2001).
J.C. Hogg et al., *The New England Journal of Medicine* vol. 350, pp. 2645-2653 (2004).
E. Hey., Neonatal Formulary 5: Drug Use in Pregnancy and the First Year of Life (2007).
H.Y.Park, et al., BMJ, (2012); 345:e6843.
Medicines Compendium 2004, entries for Symbicort 100/6 and Symbicort 200/6.
C.L. Leach et al., Eur. Respir. J., vol. 12, pp. 1346-1353 (1998).
Szafranski et al, Efficacy and safety of budesonide/formoterol in the management of chronic obstructive pulmonary disease, Eur Respir J 2003, 21: 74-81.
Tashkin et al, Drugs 2008; 68(14); 1975-2000, "Efficacy and safety of Budesonide and Formoterol in one pressurized meterd-dose inhaler in patients with moderate to very severe chronic obstructive pulmonary disease", (2008).
Bousquet et al, Elsevier Respiratory Medicine (2007) 101, 2437-2446. "Budesonide/formoterol for maintenance and relief in uncontrolled asthma vs. high-dose salmeterol/fluticasone", (2007).
Leader, D. "treatment for Severe COPD" accessed on Oct. 13, 2011, at copd.about/com/od/copdtreatment/a/Treatment-For_severe-Copd.htm?p=1.
Vippagunta et al. "Crystalline Solids," Advanced Drug Delivery Reviews, 2001, 48, pp. 3-26.
Braga et al. (Chem. Commun., "Making Crystals from Crystals: a green route to crystal engineering and polymorphism," 2005, pp. 3635-3645.
Seddon, K.R., "Pseudopolymorph: a polemic, "Crystal Growth & Design, 2004, 4(6), pp. 1087, web release date Oct. 19, 2004.
Online Merck Manual of Medical Information, $2^{nd}$ Edition, Alpha-1-Anti-typsin Deficiency, accessed on Apr. 23, 2011 at www.merck/manuals.com/home/print/sec04/ch045b.html.
Mario, P.S. and Ind, P.W.., Scientific evidence and expert clinical opinion for the selection of bronchodilators: clinical decision making in the individual patient, In "Effective Management of Chronic Obstructive Pulmonary Disease," Chapter 5 (Wedzicha J. Ind PW, et al. eds, 2001), Aexculapius Medical Press: London, 2001, pp. 3-23.
Global Initiative for Chronic Obstructive Lung Disease, MCR Vision, Inc., 2006.
Notification of Reexamination dated Aug. 21, 2019 issued in corresponding Chinese patent application 201610483860.4.
Bergman—"20 Common Problems in Pediatrics", Higher Education Press, Mar. 2003, $1^{st}$ edition; pp. 164-165, the section "Asthma", tables 14-18 (10 pages).
Jiatai—"Clinical Pharmacology" People's Medical Publishing House, Feb. 1998, $2^{nd}$ edition, p. 1122 (14 pages).
Bin—"Practical Handbook of New Drugs", People's Medical Publishing House, Sep. 1999, $1^{st}$, edition, p. 517-518, the section "2.4 Glucocorticosteroids" (3 pages).
Xiang "Guidelines on the Use of Medicines for Children", JinDun Publishing House, Mar. 2010, p. 230 (9 pages).

\* cited by examiner

Figure 1: Cumulative % Undersize BDP and FF Mass Distributions
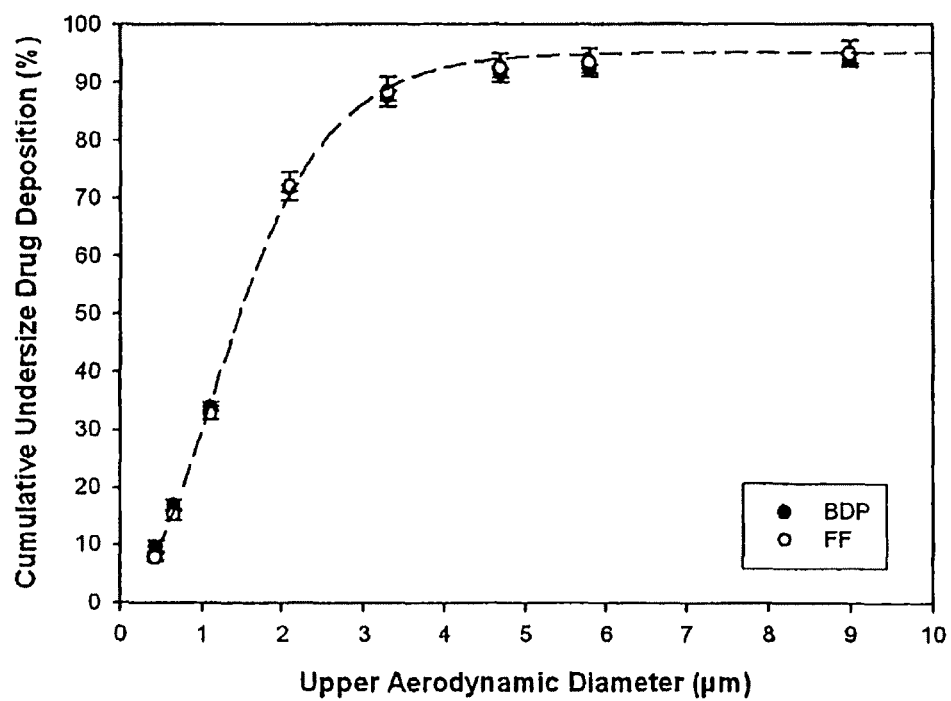

Figure 2: Percentage (of Metered Dose) ACI Stage by Stage deposition of LABA and ICS. Bars represents Mean ±SD; (n=6)
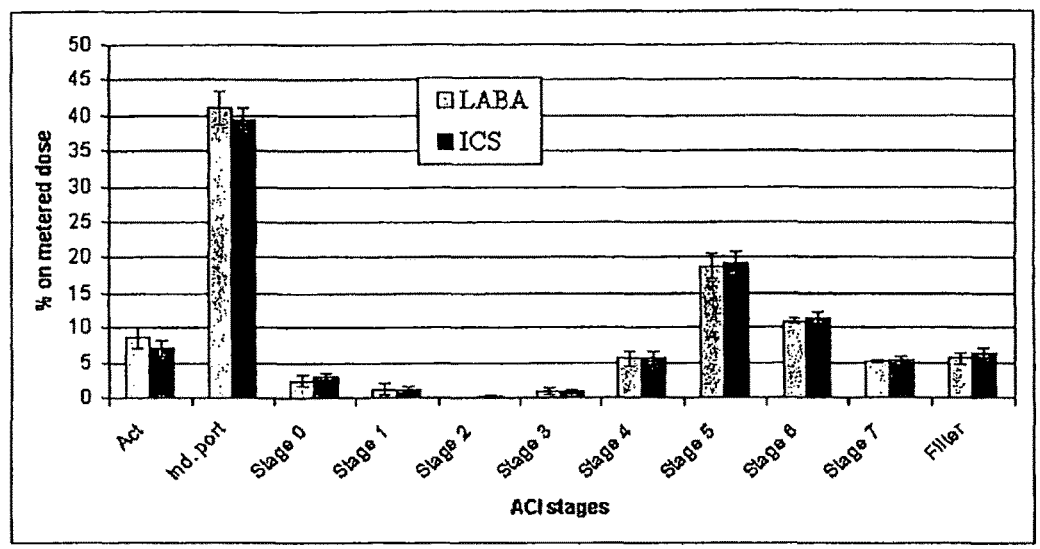

PHARMACEUTICAL SOLUTION FORMULATIONS FOR PRESSURISED METERED DOSE INHALERS

CROSS REFERENCES TO RELATED APPLICATIONS

This application is a continuation of International Patent Application No. PCT/EP2007/003420, filed on Apr. 19, 2007, and claims priority to U.S. patent application Ser. No. 11/408,026, filed on Apr. 21, 2006, both of which are incorporated herein by reference in their entireties.

BACKGROUND OF THE INVENTION

Field of the Invention

The present invention relates to methods for the prevention or treatment of a severe broncho-pulmonary disease by administering a solution formulation from pressurized metered dose inhalers (pMDIs) which is cable of providing therapeutic doses of two or more active drug substances to the lungs, in which substantially all of the liquid particles emitted on actuation of the inhaler contain the two or more active drug substances in a ratio which is substantially the same as a predetermined ratio of the two or more active drug substances in the medicament and the two or more active drug substances are delivered with substantially the same particle size distribution.

Discussion of the Background

Treatment of broncho-pulmonary diseases such as asthma and chronic obstructive pulmonary disease (COPD) with inhaled aerosol drugs offers advantages over systemic therapy, including a more rapid onset and reduced adverse effects, because of the direct targeting of the lungs.

Pressurised metered dose inhalers (pMDIs) are well known devices for administering pharmaceutical products to the respiratory tract by inhalation. MDIs use a propellant to expel droplets containing the pharmaceutical product to the respiratory tract as an aerosol. Formulations for aerosol administration via MDIs can be solutions or suspensions. Solution formulations offer the advantage of being homogeneous, with the active ingredient and excipients completely dissolved in the propellant vehicle or its mixture with one or more suitable co-solvents such as ethanol. Solution formulations also obviate the physical stability problems associated with suspension formulations thereby assuring more consistent uniform dosage administration.

Drugs commonly delivered by inhalation for treating broncho-pulmonary diseases include short-acting and long-acting beta$_2$-agonists, anticholinergics/antimuscarinic agents, and corticosteroids in hydrofluoroalkane (HFA) propellants.

In particular, long-acting $\beta_2$-agonists (LABAs) such as formoterol and salmeterol and antimuscarinic agents, such as selective muscarinic receptors 3M antagonists, in combination with inhaled corticosteroids (ICS), have been proposed for the prevention and/or treatment of said diseases. However, despite modern maintenance treatments, some patients are still under treated particularly when the broncho-pulmonary disease is in a severe form.

Hence there is still an unmet need for medicaments more efficacious for the prevention or treatment of severe forms of broncho-pulmonary diseases, in particular of sever forms of asthma and COPD.

SUMMARY OF THE INVENTION

Accordingly, it is one object of the present invention to provide novel medicaments which are useful for the prevention and/or treatment of severe forms of broncho-pulmonary diseases, in particular of severe forms of asthma and COPD.

It is another object of the present invention to provide novel novel methods for the prevention and/or treatment of severe forms of broncho-pulmonary diseases, in particular of severe forms of asthma and COPD.

These and other objects, which will become apparent during the following detailed description, have been achieved by the inventors' discovery that more efficacious medicaments are obtained by providing pressurized solution formulations of two or more drug substances that, upon actuation of the inhaler deliver the active drug substances in a ratio which is substantially the same as the predetermined ratio of said active drug substances in the medicament and the active drug substances are delivered with substantially the same particle size distribution.

In this way a co-deposition within the lung of the combination of the active drug substances is obtained which results in a clinical response of lung function that is greater than the sum of the response of the individual drugs administered.

Thus, the present invention provides methods for the prevention and/or treatment of a severe broncho-pulmonary diseases, which comprise administering a pressurized solution formulation from a metered dose inhaler, which contains two or more active drug substances in a predetermined ratio dissolved in an HFA propellant and ethanol as a co-solvent, wherein, on actuation of the inhaler, substantially all of the liquid particles emitted contain the two or more active drug substances in a ratio which is substantially the same as the predetermined ratio of the two or more active drug substances in the medicament and the two or more active drug substances are delivered with substantially the same particle size distribution.

The present invention also provides methods of preventing and/or treating a severe broncho-pulmonary disease, which comprise administering a combination of two or more active drug substances to the lung region tract of a subject by actuation of a pressurized single metered dose inhaler which contains the two or more active drug substances in a predetermined ratio and dissolved in an HFA propellant and ethanol as a co-solvent, wherein, on actuation of the inhaler, substantially all of the liquid particles emitted contain the two or more active drug substances in a ratio which is substantially the same as the predetermined ratio of the two or more active drug substances and the two or more active drug substances are delivered with substantially the same particle size distribution.

The present invention further provides methods of preventing and/or treating a severe broncho-pulmonary disease, which comprise administering a pressurized solution formulation from a metered dose inhaler, which contains two or more active drug substances in a predetermined ratio dissolved in an HFA propellant and not more than 20% w/w ethanol as a co-solvent, wherein, on actuation of the inhaler, substantially all of the liquid particles emitted contain the two or more active drug substances in a ratio which is substantially the same as the predetermined ratio of the two or more active drugs and the two or more active drug substances are delivered with substantially the same particle size, thereby improving the co-deposition of said drugs in the lung tract of a patient and therefore their synergistic interaction.

The present invention also provides metered dose inhalers, which contain two or more active drug substances in a predetermined ratio dissolved in an HFA propellant and ethanol as a co-solvent, wherein, on actuation of the inhaler, substantially all of the liquid particles emitted contain the two or more active drug substances in a ratio which is substantially the same as the predetermined ratio of the two or more active drug substances and the two or more active drug substances are delivered with substantially the same particle size distribution.

The present invention also provides pressurized single metered dose inhalers which contain two or more active drug substances in a predetermined ratio and dissolved in an HFA propellant and ethanol as a co-solvent, wherein, on actuation of the inhaler, substantially all of the liquid particles emitted contain the two or more active drug substances in a ratio which is substantially the same as the predetermined ratio of the two or more active drug substances and the two or more active drug substances are delivered with substantially the same particle size distribution.

The present invention further provides metered dose inhalers, which contain two or more active drug substances in a predetermined ratio dissolved in an HFA propellant and not more than 20% w/w ethanol as a co-solvent, wherein, on actuation of the inhaler, substantially all of the liquid particles emitted contain the two or more active drug substances in a ratio which is substantially the same as the predetermined ratio of the two or more active drugs and the two or more active drug substances are delivered with substantially the same particle size, thereby improving the co-deposition of said drugs in the lung tract of a patient and therefore their synergistic interaction.

Preferably the active drug substances comprise a bronchodilating and/or anti-inflammatory compound, more preferably a long acting beta$_2$-agonist and an inhaled corticosteroid.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows the cumulative % undersize BDP and FF mass distributions for the sample as determined in Example 1; and FIG. 2 shows the percentage (of metered dose) ACI stage by stage deposition of LABA and ICS (bars represents Mean±SD; (n=6)) as measured in Example 2.

DETAILED DESCRIPTION OF THE PREFERRED EMBODIMENTS

As used herein the expression "on actuation of the inhaler, substantially all of the liquid particles emitted contain the two or more active drug substances in a ratio which is substantially the same as the predetermined ratio of the two or more active drug substances" means that the relative standard deviation (RSD) of the ratio of the amounts of drugs measured along the stages of an Andersen Cascade Impactor (ACI) is less than 5.0%, preferably less than 3.5%, more preferably less than 2.0%, when the active drug substances are delivered at doses comprised between 4 and 16 µg, while it is less than 15%, preferably less than 12%, when at least one of the active ingredient is delivered at a dose higher than 0.5 but lower than 4 µg. This is because, from an experimental standpoint, it is more difficult to determine the ratio in a precise way when one or more of the active ingredients is delivered at a low dose.

The relative standard deviation (RDS) is calculated by the formula:

$$(SD/mean)*100.$$

As used herein the expression "the two or more active drug substances are delivered with substantially the same particle size" means that the particle size distributions of the drugs determined along the stages of the Andersen Cascade Impactor (ACI) are not statistically significantly different ($p<0.05$).

As used herein the term "dose" means the amount of active ingredient delivered by a single actuation of the inhaler.

As used herein, the expression "% w/w" means the weight percentage of the component in respect to the total weight of the composition.

According to the Global INitiative for Asthma (GINA), severe persistent asthma is defined as a form characterized by daily symptoms, frequent exacerbations, frequent nocturnal asthma symptoms, limitation of physical activities, forced expiratory volume in one second ($FEV_1$) equal to or less than 60% predicted and with a variability higher than 30%.

According to the Global initiative for chronic Obstructive Pulmonary Disease (GOLD) guidelines, severe COPD is a form characterized by a ratio between $FEV_1$ and the Forced Vital Capacity (FVC) lower than 0.7 and $FEV_1$ between 30% and 50% predicted. The very severe form is further characterized by chronic respiratory failure.

The particle size distribution (PSD) data of the pMDI formulations have been obtained using an Andersen Cascade Impactor (ACI) in accordance with the European Pharmacopoeia 5th Edition 2007, part 2.9.18, page 3109, and in particular according to the procedure described in detail in Example 1.

The level of co-deposition may be monitored by a scintigraphic study which permits evaluation of the distribution of the active substances along the various lung areas, i.e. from the central to the peripheral airways.

Formulations, which upon actuation of the pressurized metered dose inhaler, on evaporation of the propellant mixture, feature an average particle size of the two active ingredients equal or below 1.1 micrometer are also referred to herein as extrafine.

The medicaments of the present invention are obtained by providing solution formulations of two or more drug substances to be used with pressurized metered dose inhalers (pMDIs) that, upon actuation of the inhaler deliver the active drug substances in a ratio which is substantially the same as the predetermined ratio of said active drug substances in the medicament and the active drug substances are delivered with substantially the same particle size distribution at stages. In fact this allows achieving a co-deposition within the lung of the combination of the active drug substances which results in a clinical response of lung function that is greater than the sum of the response of the individual drugs administered. Co-deposition in the same lung region indeed maximizes the synergistic effects, with a great improvement in the lung function of the patients.

The solution formulations to be used with pMDIs of the present invention (hereinafter pressurized solution formulations), comprise an ethanol/HFA propellant based solution formulation for aerosol administration containing a combination of two or more active drug substances, wherein said active drug substances are fully dissolved in the formulation, each liquid particle generated during the MDIs atomisation process contains drug concentrations consistent with the liquid properties of the product's solution formulation and that this consistency is maintained for the residual particles following excipient evaporation.

Moreover it has been found that each droplet of the aerosol cloud emitted on actuation of the inhaler containing a solution of different active drug substances dries to give particles of the active materials with identical size distributions in the correct ratio.

This characteristic is maintained through the life of the inhaler device.

It is now surprisingly been found that the formulations described above are particularly useful for the prevention and/or treatment of a severe broncho-pulmonary disease, especially severe persistent asthma and severe COPD.

It is preferred that the solution formulation be suitable for delivering the therapeutic daily doses of the active ingredients in one or two actuations.

Advantageously the solution formulation is suitable for delivering at least one of the active ingredients at a dose lower than 20 μg. In particular, in certain embodiments, the dose of at least one of the active ingredient to be delivered shall be comprised between 4 and 16 μg, preferably 6 or 12 μg, more preferably 6 μg. In other embodiments, the dose of at least one of the active ingredient shall be higher than 0.5 but lower than 4 μg, preferably 1 or 2 μg, more preferably 1 μg.

Active ingredients which may be used in the aerosol formulations of the invention are short- and long-acting beta$_2$-adrenergic agonists, preferably long-acting beta$_2$-adrenergic agonists such as formoterol, salmeterol, indacaterol, carmoterol and salts thereof and their combinations with other active ingredients, preferably selected from the group of inhaled corticosteroids (ICS) or anticholinergic atropine-like derivatives, antimuscarinic M3 inhibitors, or phosphodiesterase 4 (PDE4) inhibitors.

Preferred ICS are beclomethasone dipropionate, budesonide and its 22R-epimer, rofleponide, ciclesonide, fluticasone propionate, mometasone furoate or triamcinolone and its ester such as triamcinolone acetonide. In a preferred embodiment, the ICS is budesonide or an epimer thereof. In another preferred embodiment, the ICS is beclomethasone dipropionate.

Preferred anticholinergic atropine-like derivatives are ipratropium bromide, oxitropium bromide, tiotropium bromide, or glycopyrronium bromide.

Preferred long acting beta$_2$-agonists are formoterol, carmoterol, and salmeterol, and salts thereof.

More preferably, the first active ingredient is a long acting beta$_2$-agonists belonging to the formula sketched below wherein R is 1-formylamino-2-hydroxy-phen-5-yl (formoterol) or 8-hydroxy-2(1H)-quinolinon-5-yl (TA 2005) or one of their salts, solvates, solvates of the salts or stereoisomers.

In a particular embodiment, the solution formulation will be suitable for delivering 6 or 12 μg/dose of formoterol fumarate, more preferably 6 μg. In another embodiment, the solution formulation will be advantageously suitable for delivering 0.5 to 4 μg/dose, preferably 0.5 to 2 μg/dose, more preferably about 1 μg/dose of carmoterol hydrochloride (TA 2005).

The ratios in which the beta$_2$-agonist and the other active drug substance may be used in the solution formulation are variable. Depending on the choice of the active drug substance, the ratios by weight which may be used within the scope of the present invention vary on the basis of the different molecular weights of the various substances and their different potencies.

Advantageously, the pressurized solutions according to the invention may contain the beta$_2$-agonist and the other active drug substance in ratios by weight ranging from 1:2 to 1:3200.

In certain embodiments, wherein the other active substance is an ICS, if the beta$_2$-agonist is delivered at a dose comprised between 4 and 16 μg, the ratio shall range between 1:3 and 1:100, preferably between 1:8 and 1:40.

In other embodiments, if the beta$_2$-agonist is delivered at a dose comprised higher than 0.5 but lower than 4 μg, the ratio by weight shall range between 1:12.5 and 1:800, preferably between 1:25 and 1:400.

When the other active drug substance present in the solution formulation is budesonide, said formulation will be suitable for delivering 50 to 400 μg/dose, preferably 100 to 200 μg/dose, more preferably 100 or 200 μg/dose, of said drug substance.

When the other active drug substance is beclometasone dipropionate, the formulation will be suitable for delivering 50 to 200 μg/dose, preferably 100 or 200 μg/dose.

The hydrofluorocarbon propellant is preferably selected from the group of HFA 134a, HFA 227, and mixtures thereof.

Advantageously the amount of ethanol in the solution formulation is comprised between 5% and 20% w/w, more advantageously between 6% and 18% w/w, preferably comprised between 8 and 16% w/w, more preferably the amount of ethanol is 12% or 15% w/w.

The solution formulation of the invention may further contain small amounts of a mineral acid to adjust the apparent pH to between 2.5 and 5.0 wherein apparent is defined in the European Patent Application No. EP 1 157 689.

Preferably the solution formulations of the present invention are capable of delivering, on actuation of the inhaler, an average fraction of particles of the active ingredients equal to or less than 1.1 micron, allowing the drugs to reach the small peripheral airways region where they exercise their pharmacological effects. Herewith the formulations featuring these characteristics will be defined as extrafine.

The solution formulations of the invention may be contained in a pressurized MDI having part of all of the internal metallic surfaces made of anodized aluminium, stainless steel or lined with an inert organic coating. Examples of preferred coatings are epoxy-phenol resins, perfluoroalkoxyalkane, perfluoroalkoxyalkylene, perfluoroalkylenes such as polytetrafluoroethylene, fluorinated-ethylene-propylene, polyether sulfone, and a mixture of fluorinated-ethylene-propylene and polyether sulfone. Other suitable coatings could be polyamide, polyimide, polyamideimide, polyphenylene sulphide, or their combinations.

According to a particular embodiment of the invention, there is provided a pressurised MDI consisting of an aluminium container filled with a formulation consisting of an extrafine solution of formoterol fumarate in combination with beclometasone dipropionate in HFA 134a as a propellant in turn containing 12% w/w ethanol as a co-solvent, the apparent pH of said solution having been adjusted to between 3.0 and 5.0 by addition of a suitable amount of hydrochloric acid.

According to a further particular embodiment of the invention, there is provided a pressurised MDI consisting of a coated container filled with a formulation consisting of an extrafine solution of 8-hydroxy-5-[(1R)-1-hydroxy-2-[[(1R)-2-(4-methoxy-phenyl)-1-methylethyl] amino] ethyl]-2(1H)-quinolinone hydrochloride (TA 2005) in combination with budesonide in HFA 134a as a propellant in turn containing 15% w/w ethanol as a co-solvent, the apparent pH of said solution having been adjusted to between 3.0 and 5.0 by addition of a suitable amount of phosphoric acid.

Advantageously, all the pressurized solution formulations of the present invention are filled in a device, such as an aerosol inhaler, according to a method comprising the following steps:

(a) preparing of a solution of one or more active ingredients in one or more co-solvents;
(b) filling of the device with said solution;
(c) optionally adding a pre-determined amount of a strong mineral acid;
(d) adding a propellant containing a hydrofluoroalkane (HFA); and
(e) crimping with valves and gassing.

The formulation is actuated by a metering valve capable of delivering a volume of between 50 μl and 100 μl.

Metering valves fitted with gaskets made of chloroprene-based rubbers can preferably be used to reduce the ingress of moisture which, as previously mentioned, can adversely affect the stability of the drug during storage. Optionally, further protection can be achieved by packaging the product in a sealed aluminium pouch.

The pressurized solution formulations having the features described in the present invention, in particular those comprising a long-acting β2-agonist (LABA) bronchodilator and an inhaled corticosteroid (ICS) are useful in the prevention and/or treatment of a severe broncho-pulmonary disease, in particular severe persistent asthma and severe and very severe chronic obstructive pulmonary disease (COPD).

Other features of the invention will become apparent in the course of the following descriptions of exemplary embodiments which are given for illustration of the invention and are not intended to be limiting thereof.

EXAMPLES

Example 1. Particle size distribution for formoterol fumarate and beclometasone dipropionate within an ethanol based solution HFA pMDI by Andersen Cascade Impactor (ACI).

The solution formulation contained beclometasone dipropionate ("BDP") (100 μg/dose) and formoterol fumarate ("FF") (dug/dose) in 50 μl in HFA 134a propellant vehicle with 12% w/w ethanol as cosolvent and 0.024% w/w hydrochloric acid (1M) as stabilizer. The formulation was packed in cans fitted with 50 μl valves and fired using a 0.30 mm actuator. Aerodynamic particle size assessments were conducted using an Andersen Cascade Impactor fitted with a USP induction port at the beginning and end of can-use life from each of two batches. Each determination was obtained by sampling 15 consecutive doses at a sampling flow rate of 28.3 l/minute. For each can tested the delivered dose was determined using DUSA methodology (Dose Unit Spray Apparatus) at the beginning, middle, and end of can-use life. Quantification of BDP and FF within test samples was performed using a HPLC method. Metered dose, delivered dose, fine particle dose, fine particle fraction, mass median aerodynamic diameter (MMAD), and geometric standard deviation (GSD) for each impactor measurement were calculated.

Aerosol performances derived from impactor measurements are summarised in Table 1. For BDP and FF respectively, the mean delivered dose values obtained from the impactor measurements were within 95 to 100% and 91 to 101% of the mean values obtained using DUSA methodology. The consistency in the fine particle fraction (both≤5 μm and≤1 μm), MMAD and GSD for BDP and FF is a consequence of the similar particle size distributions of the two drugs as shown in FIG. 1 (not statistically significantly different).

TABLE 1

Summary of Aerosol Performances. Data represents Mean ± SD; (n = 4).

| Drug | BDP | FF |
|---|---|---|
| Metered Dose, MD (μg) | 94.5 ± 2.3 | 5.4 ± 0.3 |
| Delivered Dose (μg) | 87.0 ± 2.2 | 4.9 ± 0.3 |
| Fine particle dose ≤5 μm (μg) | 34.5 ± 1.1 | 1.9 ± <0.1 |
| Fine particle fraction ≤5 μm (%) | 39.7 ± 2.2 | 38.6 ± 2.2 |
| Fine particle dose ≤1 μm (μg) | 11.1 ± 0.2 | 0.6 ± <0.1 |
| Fine particle fraction ≤1 μm (%) | 12.8 ± 0.4 | 11.8 ± 0.5 |
| MMAD (μm) | 1.4 ± <0.1 | 1.5 ± <0.1 |
| GSD | 2.0 ± 0.1 | 2.0 ± 0.1 |
| Shot Weight (mg) | 54.0 ± 1.3 | |

Table 2 presents the mean drug deposition for samples containing >5% of the metered dose, the total being representative of 94.5±5.4% of the total metered drug mass. The ratio of BDP to FF presented in Table 2, expressed as mean and standard deviation, is 17.6±0.3, which is consistent with the ratio of metered BDP and FF (17.6±0.6). The consistent ratio of the drug masses over the size fractions implies that each particle generated during the atomisation process contains drug concentrations consistent with the liquid properties of the product's solution formulation, and that this consistency is maintained for the residual particles following excipient evaporation, such that the measured particle size distributions for both resident drugs are identical.

TABLE 2

ACI stage-by-stage deposition. Data represents Mean ± SD; (n = 4).

| Deposition site | BDP (μg) | FF (μg) | | Ratio: BDP/FF |
|---|---|---|---|---|
| Actuator | 7.5 ± 0.3 | 0.43 ± 0.03 | | 17.6 |
| Induction Port | 49.5 ± 3.2 | 2.89 ± 0.23 | | 17.1 |
| Stage 4 (2.1-3.3 μm) | 5.9 ± 0.3 | 0.33 ± 0.01 | | 17.8 |
| Stage 5 (1.1-2.1 μm) | 14.2 ± 0.8 | 0.80 ± 0.03 | | 17.7 |
| Stage 6 (0.65-1.1 μm) | 6.4 ± 0.3 | 0.36 ± 0.01 | | 17.8 |
| Total: | 83.6 ± 4.9 | 4.82 ± 0.32 | Mean ± SD: | 17.6 ± 0.3 |

Example 2. Solution combination containing carmoterol hydrochloride (TA 2005) as LABA and budesonide (BUD) as ICS.

The LABA TA 2005 is present in the combination at a strength of 1 μg/dose per actuation while budesonide is present at 100 μg/dose per actuation within an acidified ethanol solution pressurized with HFA 134a. Aerodynamic assessment of fine particles was performed by sampling 10 consecutive doses from each pMDI into an ACI. The impactor was fitted with a USP induction port and operated at a sampling flow rate of 28.3 l/minute. Three pMDIs were tested (from the beginning, middle, and end of batch) and were tested at the beginning and end of life. Drug deposition within the impactor was quantified using an HPLC assay. The fine particle dose (FPD) was determined by summation of the drug collected on the ACI stages between S3 and filter.

Table 3 summarizes the deposition of TA 2005 and budesonide on the individual stages of the ACI, while Table 4 summarizes the aerosol performances. The nominal dose of the combination pMDI was 1 μg TA 2005: 100 μg budesonide. FIG. 2 summarizes these results expressed as the % metered dose.

TABLE 3

ACI stage-by-stage deposition. Data represents Mean ± SD; (n = 6).

| Deposition site | TA 2005 (μg) | BUD (μg) | Ratio: BUD/TA 2005 |
|---|---|---|---|
| Actuator | 0.08 ± 0.02 | 6.68 ± 1.14 | 83.5 |
| Induction port | 0.40 + 0.03 | 38.16 + 2.29 | 95.4 |
| Stage 4 | 0.05 ± 0.01 | 5.45 ± 0.83 | 109.0 |
| Stage 5 | 0.18 ± 0.02 | 18.5 ± 1.83 | 102.8 |
| Stage 6 | 0.11 ± 0.01 | 10.8 ± 0.75 | 98.2 |
| | | Mean ± SD: | 97.8 ± 9.5 |

TABLE 4

Summary of Aerosol Performances. Data represents Mean ± SD (n = 6).

| Drug | BUD | TA 2005 |
|---|---|---|
| Delivered Dose (μg) | 89.7 ± 3.2 | 089 ± 0.03 |
| Fine particle dose ≤5 μm (μg) | 47.1 ± 2.7 | 0.45 ± 0.03 |
| Fine particle fraction ≤5 μm (%) | 52.5 ± 2.3 | 51.0 ± 3.0 |

The results demonstrate that the solution combination of the example provides fine particle fractions for the two components which are not statistically significantly different (p<0.05), despite the significantly different concentration of the two active drugs in the aerosol cloud. The ratio between the two active drugs is maintained in all the ACI stages allowing their co-deposition in the lungs, which could offer an increased opportunity for any synergistic interaction to occur.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for the treatment of severe or very severe chronic obstructive pulmonary disease, which comprises administering to a subject in need thereof an effective amount of a pressurized solution formulation from a metered dose inhaler, which comprises two or more active drug substances in a predetermined ratio dissolved in an HFA propellant, consisting of HFA 134a and a co-solvent,
wherein, on actuation of said inhaler, substantially all of the liquid particles emitted contain said two or more active drug substances in a ratio which is substantially the same as said predetermined ratio of said two or more active drug substances and said two or more active drug substances are delivered with substantially the same particle size distribution,
wherein said solution formulation comprises formoterol or a salt thereof and beclomethasone dipropionate.

2. The method according to claim 1, wherein said formulation comprises formoterol fumarate.

3. The method according to claim 1, wherein said formulation comprises ethanol as a cosolvent in an amount between 5% and 20% w/w, based on the total weight of said formulation.

4. The method according to claim 1, wherein said subject is suffering from severe chronic obstructive pulmonary disease.

5. The method according to claim 1, wherein said subject is suffering from very severe chronic obstructive pulmonary disease.

6. The method according to claim 1, wherein said formulation consists of:
   (a) formoterol or a salt thereof;
   (b) beclomethasone dipropionate;
   (c) HFA 134a;
   (d) ethanol; and further
   (e) 1M hydrochloric acid.

7. The method according to claim 6, wherein said formulation contains formoterol fumarate.

* * * * *

UNITED STATES PATENT AND TRADEMARK OFFICE
CERTIFICATE OF CORRECTION

PATENT NO. : 10,525,006 B2
APPLICATION NO. : 15/353978
DATED : January 7, 2020
INVENTOR(S) : Lewis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 15 days.

Signed and Sealed this
First Day of June, 2021

Drew Hirshfeld
*Performing the Functions and Duties of the
Under Secretary of Commerce for Intellectual Property and
Director of the United States Patent and Trademark Office*